(12) United States Patent
Ewert et al.

(10) Patent No.: US 8,977,358 B2
(45) Date of Patent: Mar. 10, 2015

(54) INTELLIGENT SELF-ORGANIZING ELECTRODE STIMULATION DELIVERY SYSTEM

(71) Applicants: NDSU Research Foundation, Fargo, ND (US); University of North Dakota, Grand Forks, ND (US)

(72) Inventors: Daniel Ewert, Lake Park, MN (US); Benjamin Braaten, Fargo, ND (US); Cody Satterlee, Blaine, MN (US); Brian Schwandt, Fargo, ND (US); Sheyann Harrison, Colorado Springs, CO (US); Christopher Yost, Seaside, CA (US); Joshua Wynne, Fargo, ND (US)

(73) Assignees: NDSU Research Foundation, Fargo, ND (US); University of North Dakota, Grand Forks, ND (US)

( * ) Notice: Subject to any disclaimer, the term of this patent is extended or adjusted under 35 U.S.C. 154(b) by 0 days.

(21) Appl. No.: 14/066,411

(22) Filed: Oct. 29, 2013

(65) Prior Publication Data
US 2014/0128932 A1 May 8, 2014

Related U.S. Application Data

(63) Continuation of application No. PCT/US2012/036645, filed on May 4, 2012.

(60) Provisional application No. 61/483,463, filed on May 6, 2011.

(51) Int. Cl.
| | | |
|---|---|---|
| *A61N 1/00* | (2006.01) | |
| *A61N 1/365* | (2006.01) | |
| *A61N 1/375* | (2006.01) | |
| *A61N 1/378* | (2006.01) | |
| *A61N 1/362* | (2006.01) | |
| *A61N 1/372* | (2006.01) | |
| *A61N 1/368* | (2006.01) | |

(52) U.S. Cl.
CPC ........ *A61N 1/37252* (2013.01); *A61N 1/36542* (2013.01); *A61N 1/3756* (2013.01); *A61N 1/378* (2013.01); *A61N 1/3627* (2013.01); *A61N 1/3684* (2013.01)

USPC ............................................... 607/18

(58) Field of Classification Search
CPC ............ A61N 1/3627; A61N 1/36542; A61N 1/37252; A61N 1/378; A61N 1/36585; A61N 1/37211; A61N 1/37217; A61N 1/37223
USPC ............................................... 607/18
See application file for complete search history.

(56) References Cited

U.S. PATENT DOCUMENTS

| | | | |
|---|---|---|---|
| 5,254,997 A | | 10/1993 | Cohn |
| 6,141,588 A | * | 10/2000 | Cox et al. ........................ 607/9 |

(Continued)

FOREIGN PATENT DOCUMENTS

WO        2012/154599 A2        11/2012

OTHER PUBLICATIONS

Korean Intellectual Property Office, International Search Report and Written Opinion issued on Nov. 30, 2012 for corresponding international patent application No. PCT/UC2012/036645, published as WO 2012/154599, pp. 1-12, with claims searched pp. 13-20 (pp. 1-20).

*Primary Examiner* — George Manuel
(74) *Attorney, Agent, or Firm* — John P. O'Banion

(57) ABSTRACT

An electrode stimulation delivery system is described having a unit and a network of wireless remote electrodes configured for implantation within a plurality of spaced apart locations in the tissue, e.g. myocardium, of a patient. The control unit is configured to be positioned at or subcutaneous to the patient's skin, and includes a processor, an antenna configured for delivering RF energy in proximity to the plurality of wireless remote electrodes, and programming executable on the processor for wirelessly communicating to the network of wireless remote electrodes via the delivered RF energy to individually control pacing of the plurality of wireless remote electrodes. Each of the plurality of wireless remote electrodes comprises a metamaterial-based biomimetic harvesting antenna comprising a Van Atta array zero-phase transmission lines to receive the RF energy to power activation of the plurality of wireless remote electrodes.

40 Claims, 12 Drawing Sheets

(56) References Cited

U.S. PATENT DOCUMENTS 7,542,804 B2 * 6/2009 Mandell .................. 607/48
2003/0229382 A1 12/2003 Sun et al.
2006/0085041 A1 4/2006 Hastings et al.
2010/0109966 A1 5/2010 Mateychuk et al.

* cited by examiner

INTELLIGENT SELF-ORGANIZING ELECTRODE STIMULATION DELIVERY SYSTEM

CROSS-REFERENCE TO RELATED APPLICATIONS

This application is a 35 U.S.C. §111(a) continuation of PCT international application number PCT/US2012/036645 filed on May 4, 2012, incorporated herein by reference in its entirety, which is a nonprovisional of U.S. provisional patent application Ser. No. 61/483,463 filed on May 6, 2011, incorporated herein by reference in its entirety. Priority is claimed to each of the foregoing applications.

The above-referenced PCT international application was published as PCT International Publication No. WO 2012/154599 on Nov. 15, 2012 and republished on Feb. 21, 2013, which publications are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to a self-organizing electrode stimulation network, and more particularly to a self-organizing electrode stimulation network and methods for cardiac resynchronization therapy.

2. Description of Related Art

When the heart as a pump is unable to meet the needs of the body, heart failure (HF) is said to be present. HF is a major cause of morbidity and mortality in the developed countries, and has an important impact on economic productivity, as it leads to substantial absenteeism and hospitalizations. About 5 million people in this country have HF, and over half a million are diagnosed with HF each year! It is the primary reason for 12 to 15 million office visits to health care providers each year, and it accounts for over 6 million hospital days/year. HF is the single most common reason for hospitalization in the Medicare database (composed principally of patients over the age of 65 years), and Medicare spends more dollars on HF management than on any other diagnosis. The prevalence of HF in the population has increased over time, especially in the elderly and truly elderly (>85 years) groups.

HF may result from a failure of the contractile pumping action of the heart (systolic HF), or conversely by an inability of the heart to fill with blood normally despite preserved contractile function (diastolic HF). While both forms of HF may be devastating in their manifestations, systolic HF has, until recently, attracted substantially more interest; perhaps as a consequence, there is now good evidenced-based data to support the use of specific pharmacologic therapies to improve not only symptoms but also morbidity and mortality due to systolic HF.

Standard pharmacologic therapy for heart failure has become standard place over the last several decades. Beta adrenergic blockers, angiotension converting enzyme inhibitors and/or angiotension receptor blockers, aldosterone antagonists, loop diuretics, and digoxin in some settings have been shown to ameliorate symptoms and/or reduce mortality in HF. The risk of death has also been reduced by the implantation of an internal cardioverter defibrillator (LCD) in appropriate candidates. Yet, despite optimal medical therapy, some patients remain symptomatic, a few of the end-stage patients are fortunate to undergo cardiac transplantation.

A promising avenue for patients who are not candidates for heart transplantation is cardiac resynchronization therapy (CRT). After FDA approval in 2001, a steady growth has occurred in cardiac resynchronization therapy (CRT) for the treatment of heart failure. As early as 2004, over 40,000 units were implanted in the U.S. alone with growth predicted for the future.

CRT uses a special pacemaker to improve the pumping action of the heart. When the heart becomes damaged and its pumping function impaired, the pumping chambers may contract in an uncoordinated and dyssynchronous manner that is inefficient and generally ineffective.

It has been shown that if both the right and left ventricles are paced simultaneously, the amount of uncoordinated pumping action is reduced, and the output from the left ventricle improves. Previously, the only way to deliver the requisite electric stimulation to "resynchronize" the heart was by the use of a specially configured pacemaker that was implanted under the skin using time-honored pacemaker techniques.

Using existing methods, two pacing leads are commonly attached using hard-wired connections to the pacemaker generator box, one positioned in the right and the other in the left ventricle (actually, the left ventricular lead is placed in a cardiac vein that runs on the surface of the heart, but biventricular pacing is achieved nonetheless). However, approximately 50% of patients do not respond to this approach, due to damages in the muscle tissue of the heart which create uneven or dyssynchronous pumping conditions (mechanical dys-synchrony), or which prevent electrical (pacing) signals from traveling through the muscle tissue to the proper location.

It is believed that existing CRT methods do not effectively depolarize regions of contractile myocardial tissue that are electrically isolated, and are not effective if different regions of the myocardium need to be sequentially depolarized at different times for an effective contraction to occur.

While the reasons for non-response have many factors, multiple endocardial pacing electrodes may be able to normalize nearly any derangements of dys-synchronous contraction. Thus, more pacing sites may result in effective therapy for some of these non-responders.

However, existing CRT methods require the use of leads to electrically connect the electrodes to the central control, which limits the number of electrodes implanted. Also existing CRT methods require the use of an implanted case with a battery. Furthermore, placing more leads in the heart can cause complications such as blood clots, altered flow patterns, and higher probability of lead mechanical failure. These complications become more critical in pediatric patients due to smaller heart anatomy.

Accordingly, an object of the present invention is a self-organizing system and means for stimulating multiple locations in a biological tissue (such as a heart muscle) which can coordinate the timing of the stimulation at these multiple locations separately in order to optimize the desired performance or condition of the biological tissue. Another object is a real-time system for evaluating ventricular contractility in a safe, effective, and reproducible way to restore ventricular function. At least some of these objectives will be met in the description provided below.

BRIEF SUMMARY OF THE INVENTION

An aspect of the present invention is a heart failure (HF) pacing therapy system incorporating multiple wireless and battery-less electrode networks with the ability to self-optimize cardiac performance over a wide range of conditions. The electrodes within the network are configured to harvest energy for their operation, collect relevant physical data in real time, and communicate with each other to optimize cardiac function for each individual patient.

The self-organizing, adaptive network of wireless and battery-less energy harvesting electrodes of the present invention provide cardiac resynchronization therapy for current technology non-responders and also provides more effective treatment for existing responders.

Another aspect is an intelligent self-organizing leadless electrode stimulation delivery system comprising a network of leadless cardiac electrodes, which acquire their necessary energy to operate from radio frequency identification (RFID) technology and metamaterial and biomimetic antennae characteristics.

By using the energy-harvesting, metamaterial-based electrodes of the present invention, the energy requirements of the system are reduced, and the need for an electrode battery is eliminated, thereby allowing multiple wireless and battery-less electrodes to be permanently implanted in the myocardium.

In another embodiment, each remote wireless electrode contains a microcontroller such that the network of microcontrollers is configured to communicate with each other. This network of electrodes is preferably configured to employ self-optimization techniques to optimize some measure of cardiac function.

In another embodiment, each wireless electrode is configured to measure a physiological characteristic of the local tissue, e.g. acceleration in Cartesian coordinates of the inner walls of the heart using accelerometers. The system is configured with programming to analyze the acquired sensor data to optimize the pacing sequence and timing using iterative, adaptive and self-organizing methods. In a preferred embodiment, the programming is configured to adapt to any dynamic change in the optimal pacing sequence and timing.

In another preferred embodiment, each remote electrode is configured to measures the acceleration, or other physiological parameter, of the inner walls of the heart using accelerometers. The system will comprise programming configured to compute a contractility index based on the plurality of remote electrode accelerations, perform a new pacing sequence based on the contractility index, and then receive a resultant index. The pacing sequence may continue to produce new measures of the index such that the programming changes its sequence and timing based on the updated data. This then results in the production of a better index over time, if one exists.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
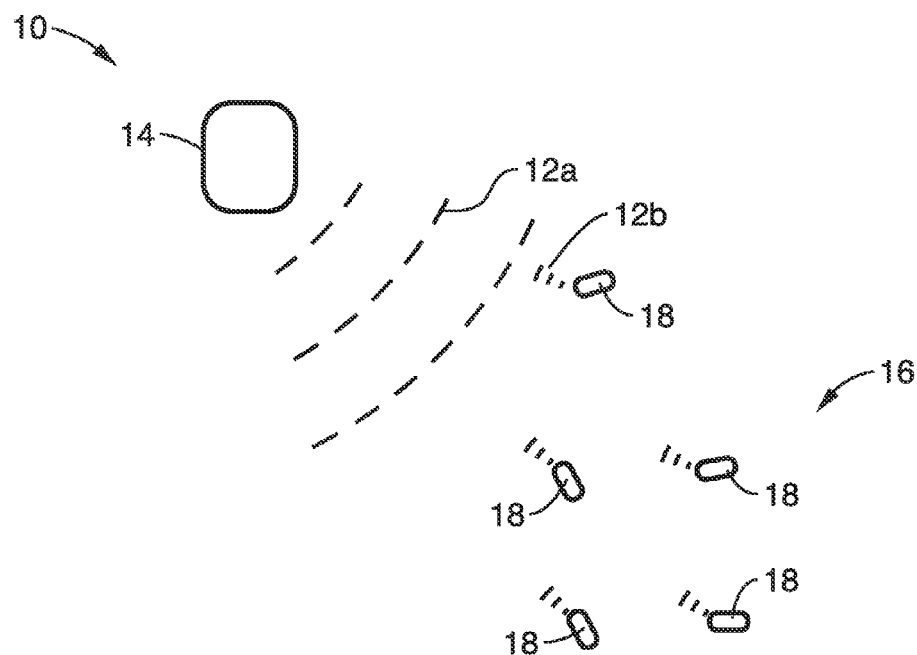
FIG. 1 illustrates a schematic diagram of a pacing therapy system incorporating a control unit configured to communicate directly with multiple wireless and battery-less electrode networks.

FIG. 1 illustrates a schematic diagram of a pacing therapy system 10 incorporating a control unit, or "can" 14 configured to communicate directly with a network 16 of wireless and battery-less electrodes 18. The can 14 is configured to radiate radio frequency (RF) energy 12a. RF energy signal 12a not only supplies energy to the remote electrodes, but also includes data that provides data to control (e.g. pacing timing, sequencing, etc.) the individual electrodes 18. The remote electrodes 18 are preferably configured to send data (e.g. sensor readings) back to the can 14 via backscatter communication signals 12b described in further detail below.

Figure 2:
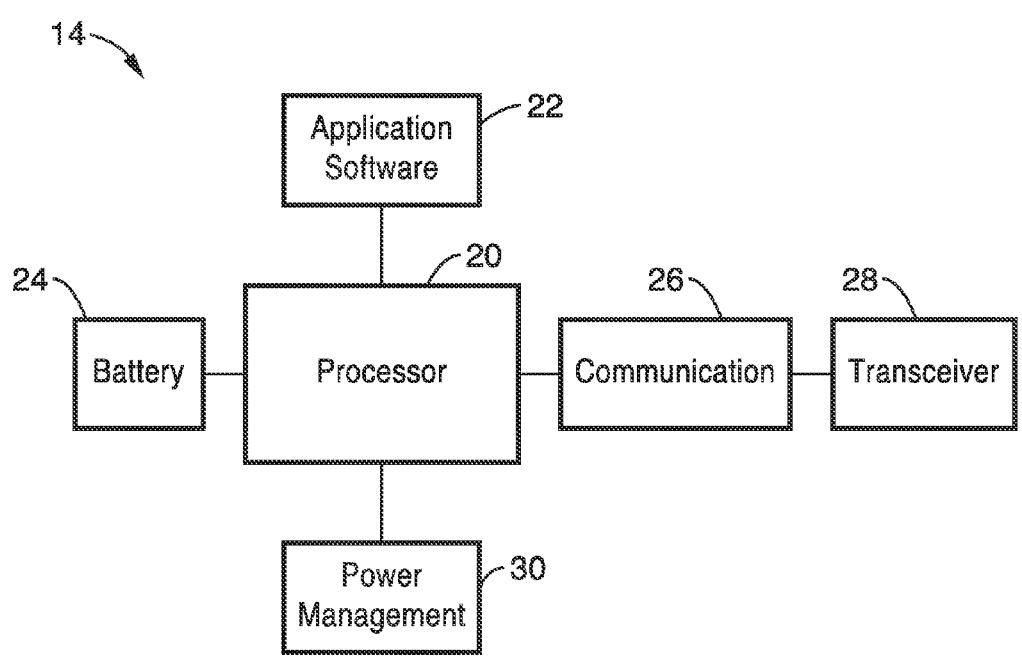
FIG. 2 illustrates a detailed diagram of the control unit of FIG. 1.

FIG. 2 illustrates a schematic diagram of the controlling electronic device, or can 14, which comprises a wireless antenna or transceiver 28 for communication and for radiating RF energy 12a to be harvested by the remote electrodes 18. The can 14 preferably comprises a processor 20 that is configured to execute the control application software 22 that drives the timing of the electrodes 18 and analyzes data received by the electrodes 18. Can 14 may further comprise communication circuitry 26 for the physician, and power management hardware 30 to extend the life of battery 24. A battery charging circuit (not shown) may also be included for allowing recharging of the battery 24.

Figure 3:
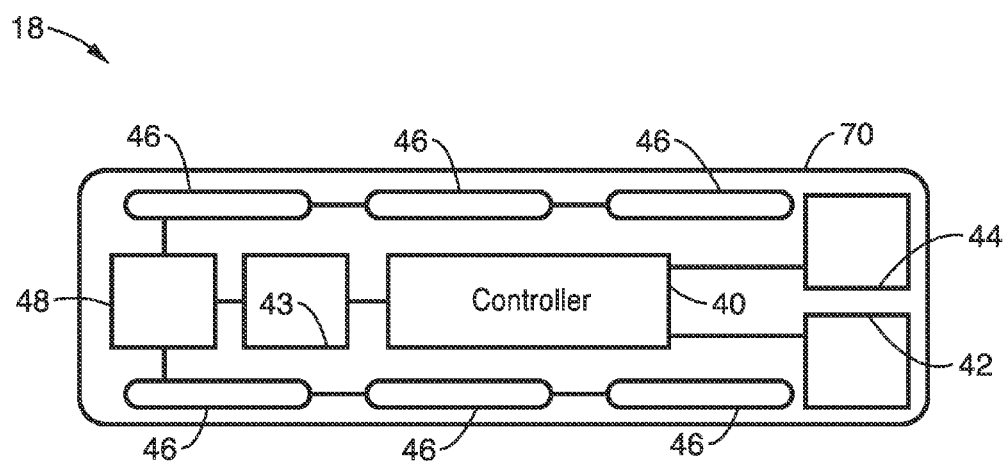
FIG. 3 shows a detailed diagram of the embedded wireless electrodes used for both configurations systems of FIG. 1 and FIG. 5.
Figure 5:
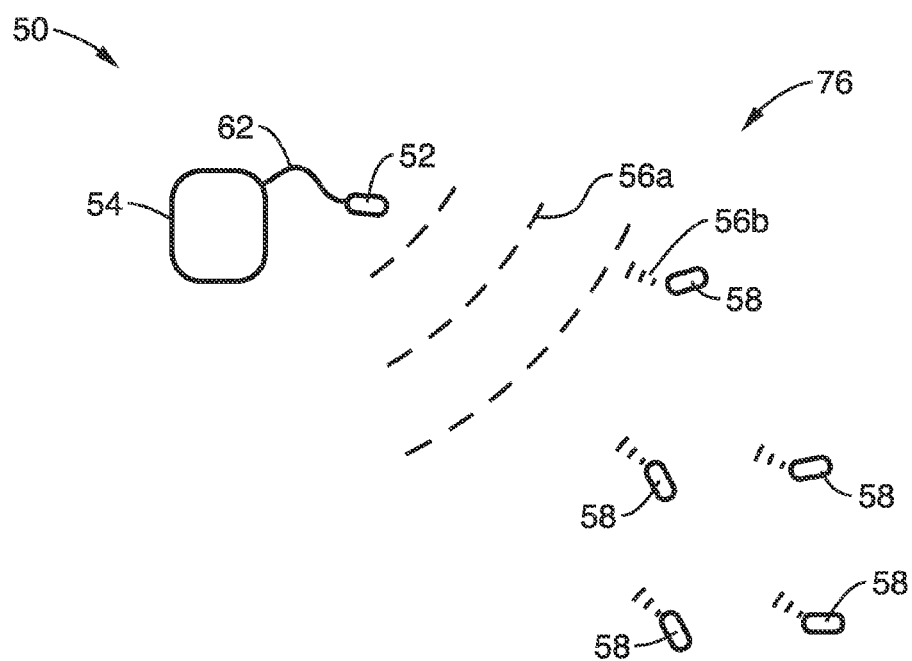
FIG. 5 illustrates a schematic diagram of a pacing therapy system incorporating a control unit with a connected electrode to communicate directly with multiple wireless and battery-less electrode networks.

FIG. 3 illustrates a schematic view of a remote pacing electrode 18 that may be used in either pacing therapy system 10 of FIG. 1 or the pacing therapy system 50 of FIG. 5. Each of the remote lead-less electrodes 18 comprise a biomimetic antenna 46 configured to harvest energy 12a distributed from the can 14 (or wired electrode 52 of the system 50 of FIG. 5). The antenna 46 is preferably constructed of metamaterial, as will be described in further detail below. The harvested energy from the antenna 46 is used to operate a low-power miniature micro-controller 40, which operates and/or acquires data from the various components within the remote electrode 18. The components are preferably housed within a casing 70 comprising a biocompatible material suitable for implantation in the human body, and in particular the heart.

The low-power miniature micro-controller 40 also sends control commands to the backscatter communication circuit 48 to send backscatter signal 12b for wireless communication from the electrode 18 to the can 14 (or backscatter signal 56b to wired electrode 52 of the system 50 of FIG. 5). The backscatter communication signal 12b/56b is achieved by changing the effective aperture of the metamaterial and biomimetic antenna 46. Backscatter communication circuit 48 will include power harvesting circuitry for harvesting power from RF signal 12a, and a sub modulating circuitry from modulating the impedance of the antenna 46 to generate the modulated backscatter signal 12b. By changing the aperture of the receiving antenna 46 between two different states, logic ones and zeros can be transmitted. By combining these two states with the timing information from the can 14, the electrode 18 is able to communicate digitally and wirelessly. Communication sub-system circuitry 43 may also be implemented for signal conditioning between the controller 40 and the backscatter communication circuit 48.

Figure 4A:
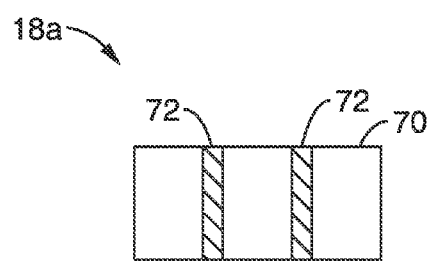
FIG. 4A illustrates an embedded wireless electrode having a pair of radial antennas.
Figure 4B:
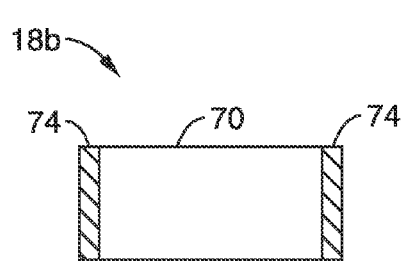
FIG. 4B illustrates an embedded wireless electrode having a pair of cap antennas.

Remote electrode 18 further comprises pacing circuitry 42, which serves as voltage storage for charging each pace, and control for pace timing, location (and magnitude, if it is deemed desirable to have such localized variation). Pacing circuitry 42 controls and delivers the voltage for the pace charge that is delivered from the remote electrode 18 into the surrounding anatomy. While this charge may be delivered by antenna 46, an additional external antenna may be employed to deliver the pacing charge. For example FIG. 4A shows a pacing electrode 18a having a pair of ring or radial pace electrodes 72 disposed around casing 70. FIG. 4B shows a pacing electrode 18b having a pair of cap pace electrodes 74 disposed at the ends of the casing 70. The pace electrodes 72/74 preferably comprise metamaterial and biomimetic antenna construction similar to that of antenna 46. Other configurations, e.g. spiral, longitudinal strips may also be contemplated in addition to the embodiments illustrated in FIGS. 4A and 4B.

For the purposes of this description, a "metamaterial and biomimetic antenna" is herein defined as an antenna which uses metamaterials and nature inspired structures to increase the performance of miniaturized (electrically small) antenna systems. The term "metamaterials" is herein defined as materials engineered with microscopic structures to produce unusual physical properties. A "biomimetic antenna" is herein defined as an antenna that uses designs based on natural structures to improve the performance. A primary purpose of the antennas of the present invention is to emit energy into free space. By incorporating metamaterials and biomimetic sub-structures, these antennas can step up the radiated power of an antenna, while still being confined to a smaller form factor that is driven by the size of the electrode acceptable for the given anatomy.

In preferred embodiments, each remote electrode 18 preferably includes one or more sensors 44 for generating feedback from the tissue surrounding the remote electrodes 18. The sensors 44 may be coupled to the biological tissue at one or more locations where the tissue is being stimulated in order to detect the movement or other desired triggered condition in the tissue. In one embodiment, the sensor 44 comprises an accelerometer (e.g. small MEMS accelerometer) that is configured to measure motion of the tissue surrounding the implanted electrode 18. For example, the sensor 44 may be coupled to muscle tissue in order to detect movement in the muscle tissue, such as the contraction of the heart. The contraction or relaxation of a muscle is only one example of a response triggered by a stimulus, and it should be noted that the present invention may be configured for detecting responses in other types of biological tissue.

Alternatively, sensor types other than motion sensors may be used to determine if a biological tissue has been stimulated. For example, a sensor which detects the electrical conditions within the tissue may indicate a change in the state of that tissue. Accordingly, sensor 44 may be configured, without limitation, to measure a number of physiological parameters, e.g. force, stress/strain (e.g. via piezoelectrics), voltage, impedance, temperature, or a combination of the above.

FIG. 5 illustrates a schematic diagram of a pacing therapy system 50 incorporating a can 54 with a connected electrode (E0) 52 (e.g. via lead wire 62). Electrode 52 is configured to communicate directly with a network 76 of wireless and battery-less electrodes 58 via emitting RF energy 56a. The remote electrodes 58 may communicate signals back to the can 54 via backscatter communication signals 56b. The electrodes 58 are similarly configured with components similar to electrodes 18 of FIG. 3, except that they are configured to communication directly with connected electrode 52 rather than can 54.

Figure 6:
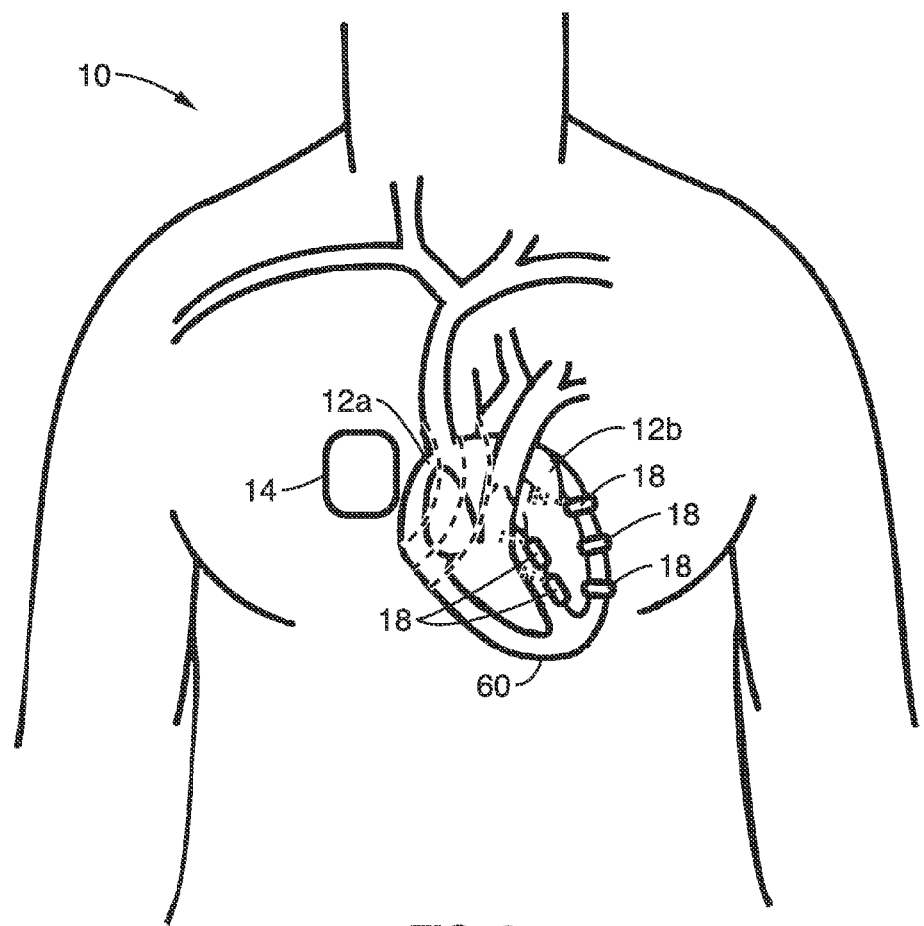
FIG. 6 illustrates a schematic diagram of the system of FIG. 1 implemented within a human heart in accordance with the present invention.

FIG. 6 illustrates a schematic diagram of the system 10 implemented within a human heart 60 of a patient as a heart pacing system. In this configuration, the can 14 may be positioned subcutaneously or adjacent to the patient's skin (e.g. chest region). The remote electrodes 18 are positioned at specific spaced apart locations within the myocardium of the heart 60. The can 14 is configured to emit RF energy 12a that travels through the patient's tissue to the implant locations of the individual remote electrodes 18, and correspondingly receive backscatter communication signals 12b from the leads.

In a preferred embodiment, system 10 of FIG. 6 comprises an intelligent self-organizing electrode stimulation delivery system. In this configuration, the pacing can 14 is located within a subcutaneous pouch, as in traditional pacing methods, and communicates pacing commands via directing RF energy 12a from the can 14 to the proximity of the heart 60. As the can 14 radiates RF energy 12a, the various lead-less cardiac electrodes 18 harvest this energy using a metamaterial and biomimetic antenna 46 to operate the low-power miniature micro-controller 40, electrode sensor 44, a pacing system 42, and a communication sub-system 43.

The sensors 44 of the remote electrodes 18 record the cardiac response to the pacing shocks and communicate this information back to the can 14 using backscattering signals 12b. The can 14 processor 20 and programming 22 uses a proprietary search algorithm 100 (described in further detail below with reference to FIG. 8) to seek a more optimum pacing timing/sequence and sends this coded information back to the multiple leadless electrodes 18 via the next pulse of RF energy 12a. This process repeats iteratively until an "optimum" pacing sequence/timing is found. The algorithm 100 may be used to continuously search for a more optimal pacing sequence/timing and can find better pacing sequences/timing as patient physiological conditions change.

Figure 7:
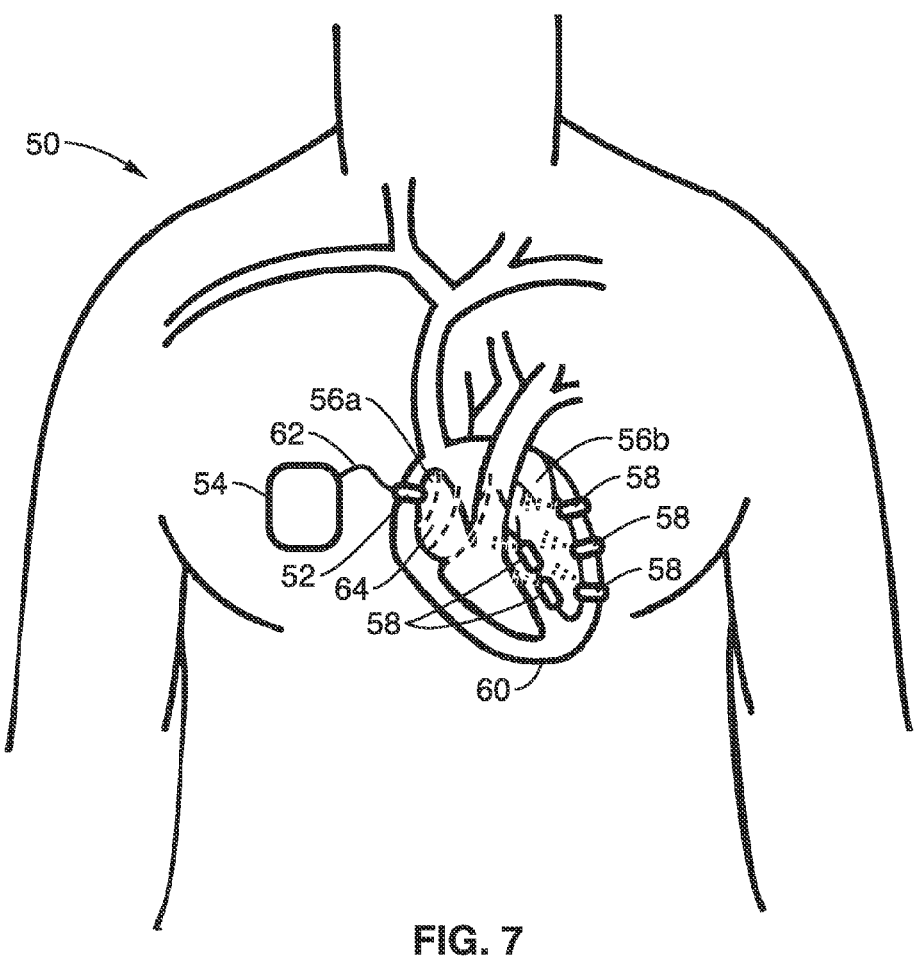
FIG. 7 illustrates a schematic diagram of the system of FIG. 5 implemented within a human heart in accordance with the present invention.

FIG. 7 illustrates a schematic diagram of the system 50 implemented within a human heart 60 of a patient as a heart pacing system. In this configuration, the can 54 may be positioned subcutaneously or adjacent to the patient's skin (e.g. chest region), and connecting electrode (E0) 52 implanted at a location within or near heart 60 (shown positioned in right atrium in FIG. 7), with lead 62 coupling the can 54 and connected electrode 52. The remote electrodes 58 are positioned at specific spaced apart locations within the wall of the heart 60 (e.g. left ventricle). The lead 62 allows for the emitted RF energy 56a to be in closer proximity to the remote electrodes 58, so that the RF energy 56a has less of the patient's tissue to travel through before reaching to the implant locations of the individual remote electrodes 58, and correspondingly less tissue for the backscatter communication signals 56b to reach the connecting electrode 52.

In a preferred embodiment, system 50 of FIG. 7 also comprises an intelligent self-organizing electrode stimulation delivery system. In this configuration, connected electrode 52 is connected to the pacing can 54 located within a subcutaneous pouch, as in traditional pacing methods. The distal tip of connected electrode 52 terminates in or near the right atrium 64. The connected electrode 52 communicates pacing commands and also directs RF energy 56a from the can 54 to the proximity of the heart. As the distal connected electrode 52 tip radiates RF energy 56a, the various lead-less cardiac electrodes 58 harvest this energy using a metamaterial and biomimetic antenna 46 to operate the low-power miniature micro-controller 40, an electrode sensor 44, a pacing system 42, and communication sub-system 43.

The electrodes 58 record the cardiac response to the pacing shocks (via the sensors 44) and communicate this information back to connected electrode 52 using a backscattering communication signals 56b, and ultimately back to the can 54 via lead 62. The can 54 processor uses a proprietary search algorithm 100 (which may comprise a module of application software 22) to seek a more optimum pacing timing/sequence, and sends this coded information back through connected electrode 52, which in turn communicates this to the multiple leadless electrodes 58. This process repeats iteratively until an "optimum" pacing sequence/timing is found. The algorithm 100 may be configured to continuously search for a more optimal pacing sequence/timing, and can find better pacing sequences/timing as patient physiological conditions change.

In a further embodiment of the system 50 of FIG. 7, each electrode 58 will pace at a specific time with respect to the connected electrode (E0) 52 that is placed in the SA node 64. The connected electrode 52 is preferably configured to sense SA node activity, and when the SA node depolarizes, the connected electrode 52 will send out a wireless signal 56a that will inform the rest of the electrodes 58 that the SA node 64 has depolarized. Alternatively, if the SA node 64 appears to not be working, the connected electrode 52 may pace the node and send out a signal to the other electrodes 58.

The signal 56a from connected electrode 52 is generally set to be the reference time. Such timing is preferred, as there ideally should be a reference time for the electrodes 58 to know when to pace. All remote electrodes thus pace with respect to connected electrode 52. Each remote electrode 58 will have a time delay to pace with respect to connected electrode 52. For instance, connected electrode 52 will send out a signal 56a and a first remote electrode 58 would have a time delay of 22 ms, a second remote electrode 58 would have a time delay of 14 ms, and so on. The network 76 would get individual localized readings of the acceleration of the heart 60 (e.g. via sensor 44 in each remote electrode 58).

Analyzing this data with programming 22, the system 50 determines new time delays for each electrode (if necessary) using an optimization scheme, performs the pace with those time delays, and then again measures the output via sensors 44. Depending on the feedback (e.g. whether it is better or worse than the previous attempts), the software 22 will determine what the next parameters will be, and what action to take. Eventually, the system 50 will discover the optimum sequence and timing.

The remote electrode arrays 16, 76 shown in FIGS. 1, and 5 through 7 detail an array of five electrodes 18, 58. However, it is appreciated that the optimal number (and placement) of pacing electrodes in the array may vary. Generally, the larger the array, the better (e.g. higher resolution within a target tissue region) the control and feedback of the electromechanical response within the target tissue region. However, the upper limit of the array population must be tempered with factors such as surgery time and complexity, morbidity of the tissue localized to the implantation, size, shape, power transmission and defective nature of the target tissue anatomy, etc.

Figure 8:
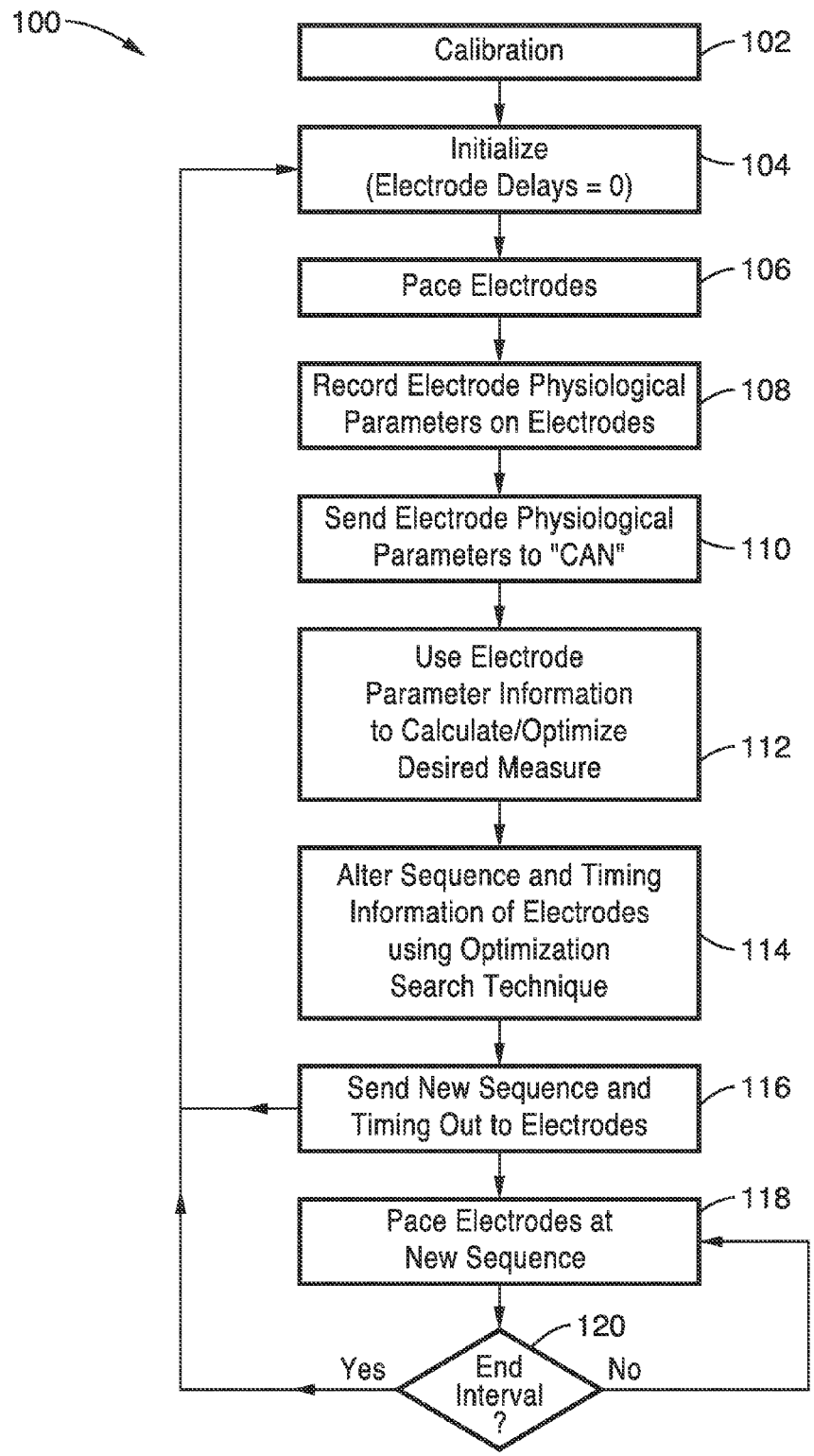
FIG. 8 illustrates the flow diagram of a search algorithm for optimizing a desired metric in accordance with the present invention.

FIG. 8 illustrates the flow diagram of a search algorithm 100 for optimizing pacing of the electrodes 18, 58 in accordance with the present invention. Algorithm 100 may be part of the application programming 22 that is included with the can 14, 54 of either system 10 or system 50.

At block 102, the system 10, 50 is first calibrated. This step is generally performed only once for a particular patient implantation. Calibration may included acquiring field strength readings from the can 14, 54, remote electrodes 18, 58, or connected electrode 52. The direction of the radiating RF energy 12a, 56a may also be tuned.

Next, at step 104, the timing of all electrodes 18, 58 in the array is initialized to pace at the same time (e.g. delay=0). The electrodes are then paced at step 106 at the specified timing. This establishes a baseline for any subsequent delay sequencing.

Generally, it is optimal to have all regions in the target region of heart 60 to be accelerating in the same or coherent manner. However, due to variations in the heart musculature, nerves, etc., the electromechanical coupling of the tissue (i.e. the mechanical response of the pace tissue as a result of a particular delivered electrical pulse) may, and often does, vary from region to region within the tissue, resulting in incoherent responses in the various tissue locales. To assess whether the desired tissue regions are acting coherently, some form of feedback is desirable for each locale.

During, and/or just subsequent to the pace at step 106, the sensor 44 records one or more physiological parameters 108 within the localized anatomy surrounding remote electrode 18, 58. In a preferred embodiment, the sensor 44 comprises an accelerometer (e.g. small MEMS accelerometer) that is configured to measure motion in Cartesian coordinates of the tissue surrounding the implanted electrode 18. Sensor 44 may be configured, without limitation, to measure a number of physiological parameters, e.g. force, stress/strain (e.g. via piezoelectrics), voltage, impedance, temperature, or a combination of the above.

At step 110, the one or more physiological parameters are sent from each remote electrode 18 back to the can 14 (or to connecting electrode 52 for electrodes 58 of system 50), via modulating the antenna 46 with backscatter communication circuit 48 to generate backscatter communication signal 12b, 56b.

The acquired sensor data is then analyzed to calculate the electromechanical response of the tissue locales specific to each electrode 18, 58 at step 112. This step determines the level of coherence, synchronicity (or ventricular dyssynchrony) between tissue locales for each electrode 18, i.e. a contractility index is computed for the target tissue region in the myocardium.

At step 114, a new timing sequence (i.e. delays for each of the electrodes 18, 58 in the array) is calculated using a greedy algorithm as the optimization search technique. The greedy algorithm follows the problem solving heuristic of making the locally optimal choice at each stage with the hope of finding a global optimum. While the greedy algorithm is a preferred embodiment, it is appreciated that other optimization algorithms may also be employed.

At step 116, the new timing sequence is sent out to the electrodes from can 14, 54 via RF signal 56a. This signal is received by each of the electrodes 18, 58, which in turn then pace at step 118. In a preferred embodiment, the pace impulse (that is sent via RF signal 56a) is a binary output, because to some degree the amplitude of the pace generally does not change the effectiveness of the pace. The pace impulse generally only needs to be large enough to depolarize the myocardium. However, if necessary, other pulse characteristics may be implemented in alternative embodiments.

The pacing at the new sequence continues for the specified interval specified in step 120. The interval may vary depending on the physician's desired protocol, the patient, or the change in activity of the patient. For example, the interval may comprise one heartbeat (in which optimization searching is performed at every pulse), every minute, hour, or day. If the end of the interval is reached, the routine returns to initialization step 104 and repeats the remaining steps in the process.

The specified interval 120 and optimization step 114 are preferably configured to adapt to changes in the status of the heart such that if the heart begins to beat faster, the system 10, 50 will adapt and pace at a faster rate, and perhaps different sequences, to increase cardiac function. Conversely, if the heart beats slower, such as at rest, then the system 10, 50 will pace at a slower rate, and perhaps a different sequence.

In the event of a remote electrode 18, 58 failure, programming 22 and algorithm 100 may be configured to reorganize itself into a new sequence and timing that optimizes cardiac function (e.g. at steps 112 and 114) based on the reduced number of pacing electrodes and feedback locations.

Because the remote electrodes 18, 58 are wireless and must be sized appropriately small for particular implant locations, generating power to operate them (e.g. to collect and analyze relevant data, perform inter-electrode communication, and pace effectively) is of particular importance.

Existing antennas used in wireless RF applications, such as rectangular microstrip and meander-line (space-filling) antennas, are particularly large, and make up a considerable portion of the overall size of typical RFID tags. Because the size of the remote electrodes 18, 58 is small for many applications (e.g. less than 1 cm in length for applications within the heart), these traditional antenna designs, if employed, drive the size of the electrode beyond an acceptable size range, and thus are prohibitive to a functioning system.

The metamaterial-based antennas 46 of the present invention are configured to have a small physical size while having properties comparable to existing larger antennas. In particular, input impedance values and radiation efficiencies of the metamaterial-based antennas 46 of the present invention are comparable to the much physically larger microstrip and meander-line antennas. Accordingly, the use of metamaterial principles are critical to function of the pacing systems 10 and 50.

Figure 9:
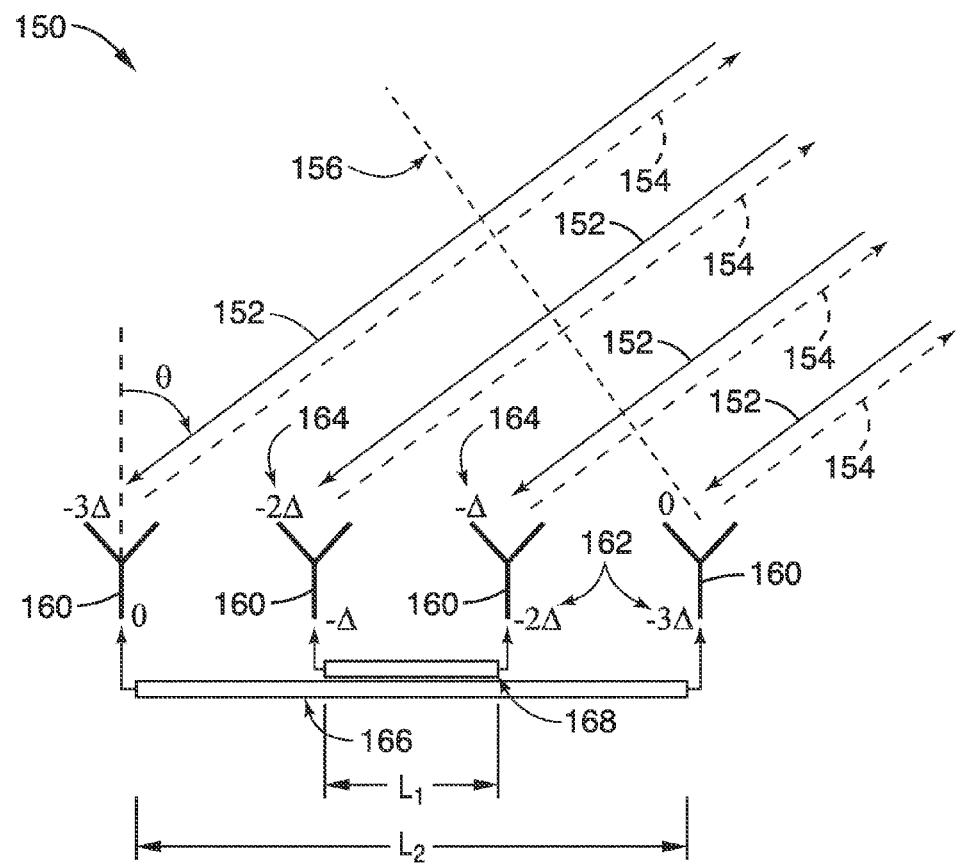
FIG. 9 shows a diagram of an exemplary Van Atta array used within the electrodes of the present invention.

FIG. 9 illustrates a schematic diagram of a metamaterial-based retrodirective (biomimetic) Van Atta array antenna configuration 150 in accordance with the present invention. The incident wave front is shown in FIG. 9 as dashed line 156, running perpendicular to incident wave lines 152 and scattered waves 154. A Van Atta array 150 can receive electromagnetic waves from arbitrary directions and scatter the electromagnetic wave in the direction of the source automatically without the addition of additional circuitry (i.e. passive steering). This is achieved by connecting the antenna elements 160 shown in pairs symmetrically about the middle of the array. The inner antenna elements 160 are coupled by a first transmission line 168 to form the receive phase 164, and the outer antenna elements 160 are coupled by a second transmission line 166 to form the transmit phase 162.

By choosing the lengths $L_1$ and $L_2$ of the connecting transmission lines 168 and 166 to be multiples of the guided wavelength of the source, the array is able to passively steer the beam in the direction of the source. By inserting diodes (not shown) along each connecting transmission line 166, 168, the array 150 can passively scan the region for microwave sources and then use the connected diodes to full-wave rectify the signal to provide a DC power for digital circuitry connected to the transmission lines 166, 168.

Figure 10:
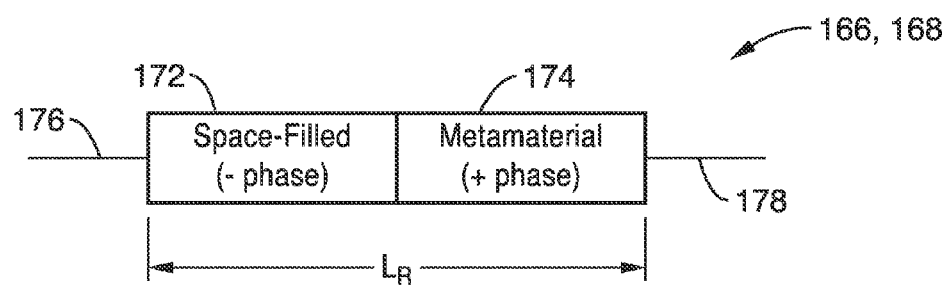
FIG. 10 shows a detailed schematic view of the zero-phase transmission lines of FIG. 9.

Referring now to the detailed schematic diagram of FIG. 10, a distinguishing feature of the array 150 of the present invention is that the connecting transmission lines 166, 168 essentially act as zero-phase transmission lines, meaning that the voltage and phase at both ends 176 and 178 of the transmission lines 166, 168 have both equal magnitude and phase.

A traditional transmission line has a negative phase constant introduced by the transmission line being a space-filling antenna construction. The array 150 of the present invention uses a cascaded-hybrid metamaterial-based transmission line segment 174 and traditional transmission line segment 172 to significantly reduce the length of the transmission lines. A traditional space-filled transmission line has a negative phase constant, while a metamaterial-based transmission line has a positive phase constant. Cascading two such transmission lines 172 and 174 in the appropriate manner, as shown in FIG. 10, results in a zero-phase transmission line (i.e., the phase introduced by the traditional transmission line is removed by the metamaterial-based transmission line). This hybrid transmission line serves to reduce the size of the transmission line length $L_R$ connecting network to the size of the physical array (approximately 0.25λ to approximately 0.50λ, or less than 1 cm in length). Therefore, by using metamaterial-based antenna elements 174 in the cascaded transmission line 166, 168 an array for backscatter communications and power harvesting can be implemented on the embedded electrodes 18, 58 smaller than 1 cm.

A common frequency band used to communicate with implanted medical devices is 401-406 MHz and the EIRP limit for a wireless device is 25 µW in each frequency bin. The bandwidth defined in the medical implant communication services (MICS) is 100 kHz and 300 kHz, which provides 28 frequency bins in the band of operation. If the transmitter (e.g. can 14, 54) is located on the surface of the body, and a wireless sensor/electrode 18, 58 is embedded in the heart 60, then the propagation loss in the body is approximately −24 dB at 402 MHz. Therefore, if the transmitter 14, 54 is driving a 3 dBi antenna with 25 µW, then 16 µW will be available for each sensor/electrode 18, 58 over each frequency bin. With 28 frequency bins, 448 µW of power will be available for the sensor array 16, 76. If a total of four sensors/electrodes 18, 58 are used in the heart, then 112 µW of power will be available for each sensors/electrode 18, 58.

Figure 11A:
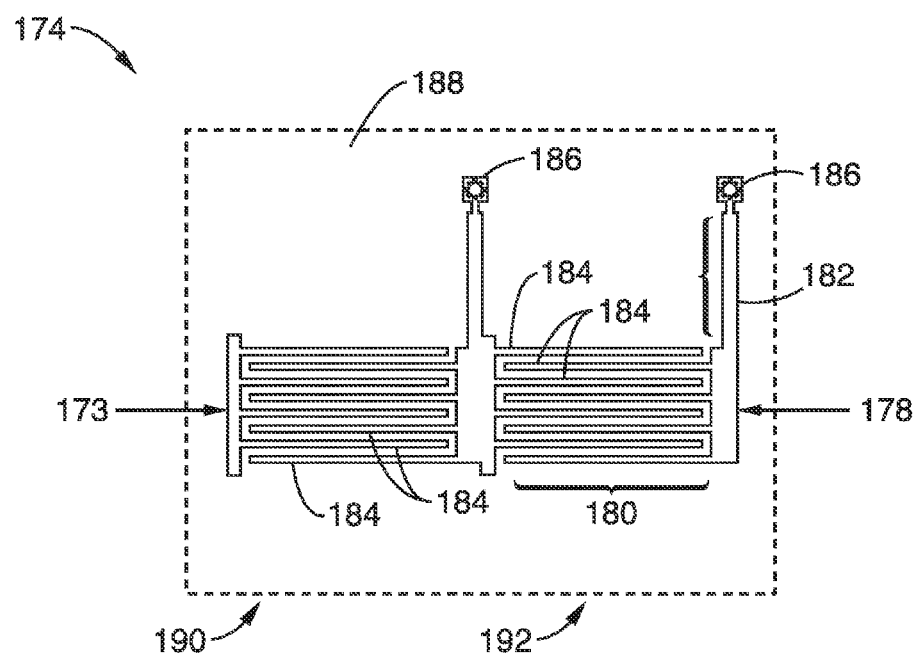
FIG. 11A shows a schematic diagram of an exemplary metamaterial-based transmission line (MTL) element comprising two cascaded metamaterial circuits.
Figure 11B:
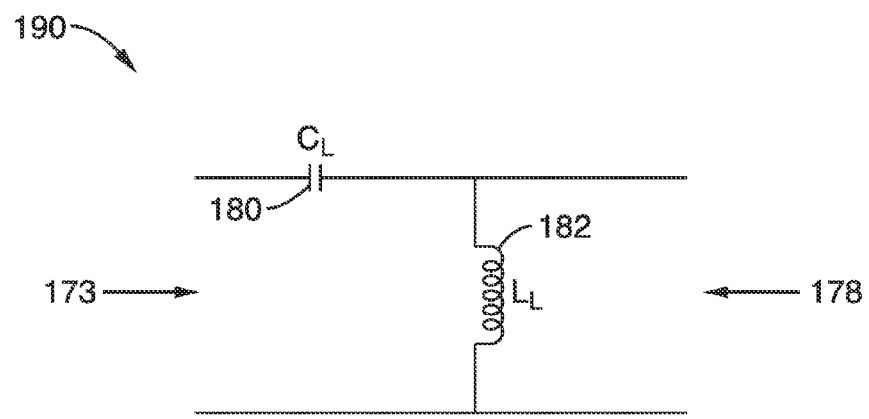
FIG. 11B shows a circuit diagram of the equivalent circuit of FIG. 11A.

FIG. 11A shows a schematic diagram of an exemplary metamaterial-based transmission line (MTL) element 174 comprising two cascaded metamaterial circuits 190 and 192. FIG. 11B shows a circuit diagram of the equivalent circuit 190 of FIG. 11A. The MTL element 174 generally comprises a series capacitance and a shunt inductance to introduce a positive phase constant. MTL element 174 comprises one or more printed conductors 190, 192 on a conformal planar surface 188. While two circuits 190, 192 are shown in the embodiment shown in FIG. 11A, it is appreciated that segment 174 may comprise one, or a number of circuits. The printed conductors 190, 192 are printed on a different layer than the printed reference plane 188. The wave from each antenna element in the Van Atta array is guided between the printed conductors 190, 192 via port 173 (coupled to the space-filled segment 172 and port 178. Capacitance segment 180 comprises interdigital capacitor fingers 184 that are used to introduce series capacitance and a printed conductor each with a via 186 connected to the reference plane 188 to introduce a shunt inductance 182.

The equivalent circuit 190 of the metamaterial is shown in FIG. 11B. A signal can be injected in port 173 and arrive at port 178, or a signal can be injected into port 178 and arrive at port 173 (a linear system).

Figure 12A:
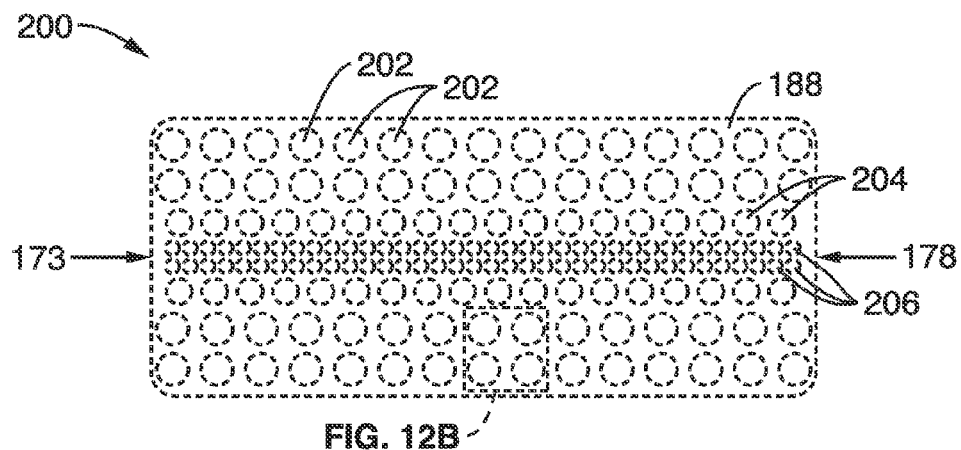
FIG. 12A shows a planar MTL structure 200 having conformal topology.
Figure 12B:
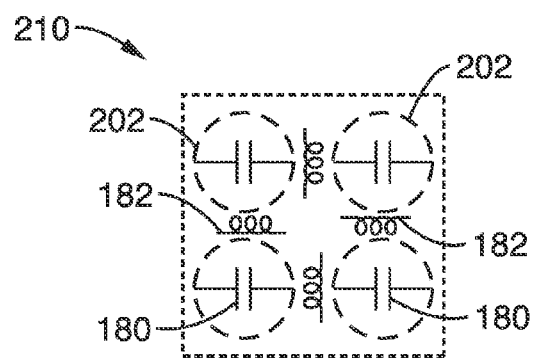
FIG. 12B illustrates the equivalent circuit 210 of a single unit cell of structure 200 shown in 12A.

FIG. 12A illustrates an alternate approach to using interdigitated capacitors and shunt inductors to realize a metamaterial transmission line. FIG. 12A shows a planar MTL structure 200 having conformal topology. This topology has a single printed conducting plane 188 printed on a conformal surface with small apertures 202, 204 and 206 of the conductor removed. The wave from each antenna element in the Van Atta array is guided on this structure 200. By removing conducting material in a particular manner, a series capacitance and shunt inductance can be introduced for a guided wave between ports 173 and 178. The equivalent circuit 210 of a single unit cell of structure 200 is shown in FIG. 12B. Each region with the removed conductor 188 (circle) can be modeled as a capacitor 180 in parallel with an inductor 182. By choosing the appropriate aperture size and spacing (e.g. large apertures 202, medium apertures 204, and small apertures 206), specific inductance and capacitance values can be introduced at various frequencies of interest. Therefore, if a wave is launched from port 173, it will immediately see conducting regions (e.g. large apertures 202) with a dominant capacitance (this introduces the required series capacitance for the positive phase advancement) and by using other regions with specific conducting regions removed near the end of the conducting plane 188, a shunt inductance (smaller apertures 206) can be introduced. Overall, the structure 200 will have the behavior of a metamaterial transmission line. While apertures 202, 204 and 206 are shown as circular openings in FIG. 12A, it is appreciated that other shapes, e.g. rectangular hexagonal, etc., may be used.

Figure 13:
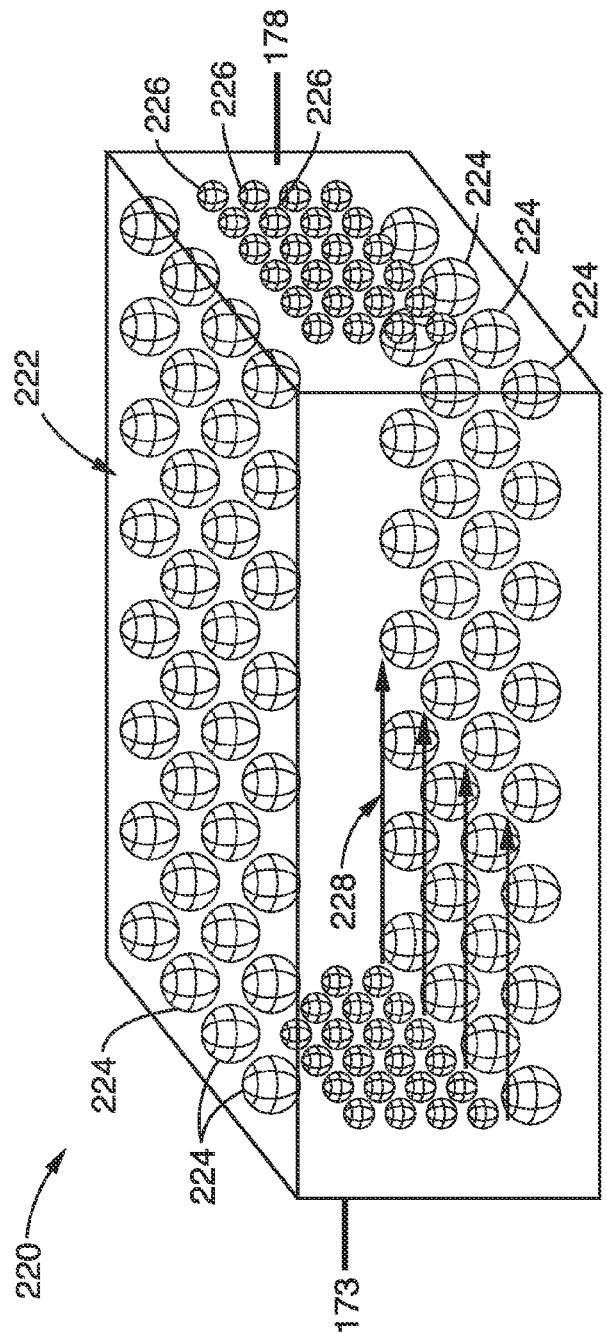
FIG. 13 shows a third MTL embodiment incorporating a 3D structure.

FIG. 13 shows a third MTL embodiment incorporating a 3D structure 220. This is a generalization of the 2D embodiment shown in FIGS. 12A and 12B, except spheres 224 and 226 are used to control the series capacitance and inductance instead of circles in the plane of the conductor. In particular, the spherical material 224 and 226 may be embedded into a 3D host material 222. The spacing and spherical sizes are adapted to determine if the region is capacitively dominant or inductively dominant. This can then be used to synthesize a 3D metamaterial transmission line that shows phase advancement and zero phase properties for the Van Atta arrays of the present invention.

If necessary, a number of energy harvesting techniques may also be used to collect additional energy from the area surrounding the heart, even from the heart itself, to power the electrodes. Two such techniques are use of accelerometers and piezoelectric devices, or piezoelectrics. An accelerometer, e.g. sensor 44, may be used to convert movement in any direction into usable electricity. Similarly, piezoelectrics may be used to turn mechanical stress into an electrical current.

Accelerometers are of particular interest, because with every heart beat, they would move and collect energy. Likewise, every time the patient moves, e.g. stands up, sits down, leans in any direction, takes a step, etc., the accelerometer can collect this energy for use of the electrodes 18, 58. When an accelerometer experiences movement, this movement is transduced into voltage. In one exemplary embodiment (not shown), if a magnet acts as a weight affected by acceleration, and a small wire is wrapped around the accelerometer, an electromagnetic field (EMF) can be produced. The energy from the EMF can be utilized by the remote electrode 18, 58 for its own uses. One exemplary accelerometer that is capable of use in the remote electrodes 18 of the present invention is a 3-axis accelerometer manufactured by, Hitachi Metals, size of 3.4 mm×3.7 mm×0.92 mm, which fits well within the dimensional parameters of the remote electrodes of the present invention, e.g. ranging 2.5 mm and 3 mm in diameter and between 6 mm and 9 mm length.

Likewise, piezoelectrics may be configured to convert the mechanical stress placed on the electrodes 18, 58 due to the contraction of the heart muscle to usable energy for the electrodes. As the electrodes 18, 58 are ideally placed directly into the myocardial muscle of the heart 60, each contraction would press on the casing 70 of the electrodes 18, 58 on all sides. In this configuration, the casing 70 of electrodes 18, 58 may be surrounded with a super-thin piezoelectric material layer (not shown) to maximize the energy harvesting capabilities of the electrodes. Piezoelectrics, like accelerometers, are also capable of collecting energy from vibrations (e.g. vibrations generated from ultrasound).

In addition to the above power-harvesting characteristics, both piezoelectrics and accelerometers are capable of collecting vital statistics about individual heartbeats (e.g. as sensors 44). By having components that have multiples uses, utility of the electrodes 18, 58 is maximized, while retaining a small size.

In another embodiment, an external back-up source of energy may be implemented that would only operate when the electrodes 18, 58 are having difficulty collecting enough energy on their own. In this embodiment, the remote electrodes 18, 58 would comprise an accelerometer (e.g. sensor 44 or an additional accelerometer dedicated to energy harvesting) configured to detect mechanical vibrations (e.g. sound) and harvest energy from them. An ultrasound transmitter/transducer (not shown) may be included in the can 14, 54 or external to the patient to provide an external back-up energy source.

Figure 14:
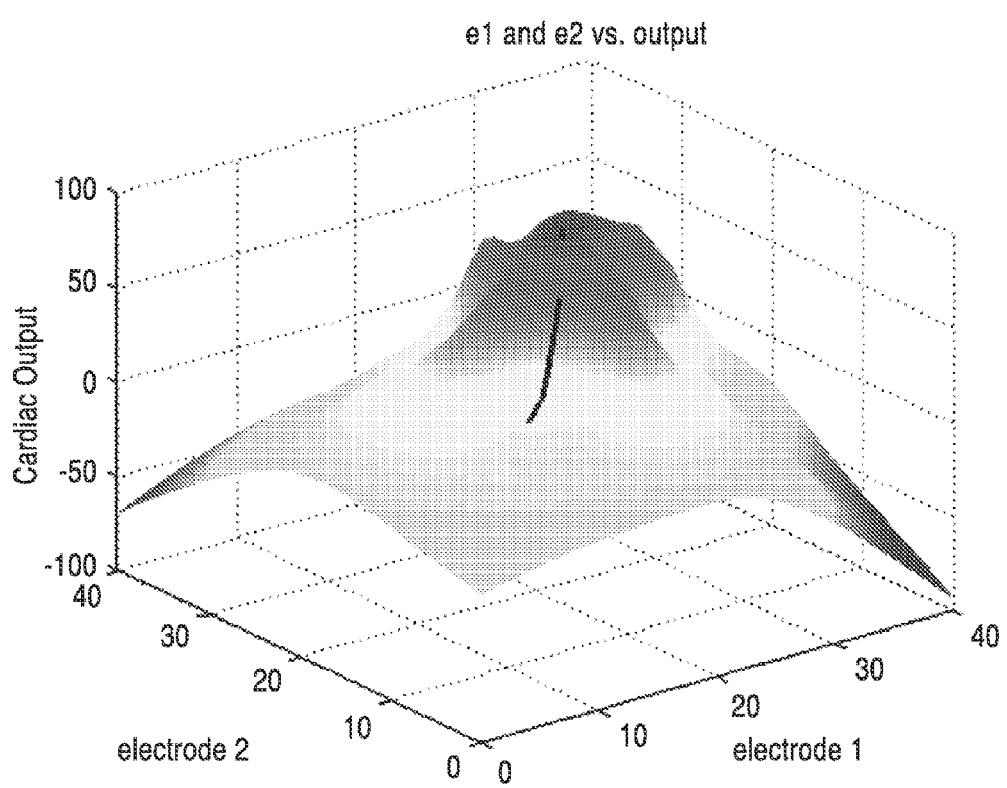
FIG. 14 shows a plot of cardiac output for a simulated search optimization algorithm with the electrode timing delays as the x and y coordinates.
Figure 15:
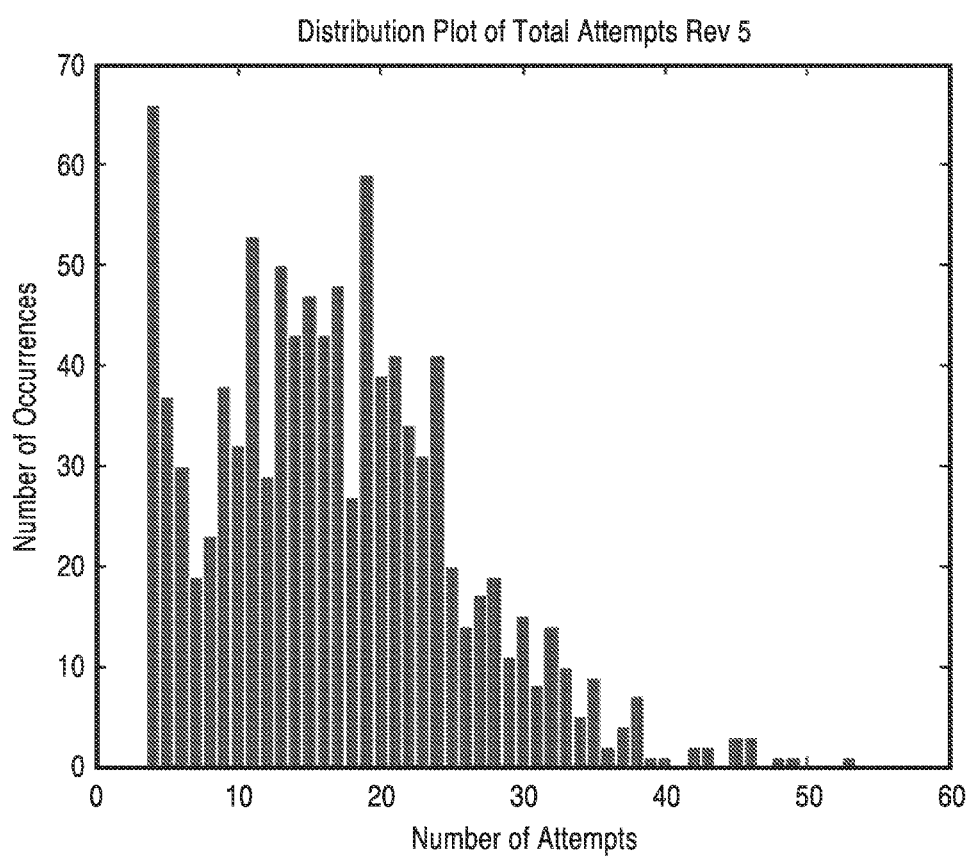
FIG. 15 shows a distribution graph of the number of attempts that it took a simulated algorithm of a method of the present invention to find an optimal output.

Referring now to FIG. 14 and FIG. 15, a simulation was performed using two pacing "nodes" having a binary output representing the pace impulse. The nodes varied their sequence and timing, and received an output for each pace. The hardware in this simulation consisted of microcontrollers working together in the scheme described above. A look-up-table of a changing cardiac function index based on pacing delays was created arbitrarily in MATLAB to produce a 3D map of how timing of each node affected cardiac function and allowed the algorithm to be tested to find a "best" cardiac function at a certain pacing delay. Each microcontroller represented a possible pacing electrode in a heart. Timing delays between two of these pacing electrodes referenced in time to another pacing electrode were varied. The self-organizing algorithm (based on the algorithm 100 shown in FIG. 8 and carried out in the reference microcontroller) then compared the heart contraction "index" for each beat over a set of beats. The maximized contraction "index" was compared to the previous maximized contraction "index" (also carried out in the reference microcontroller), and the next timing delays were sent out to a look-up-table. This system would find the look-up-table's built in optimum/"best" pacing delay for each electrode.

The tested algorithm was configured to adjust the timing delays for pacing, and was implemented in a simulated network of electrodes to optimize the cardiac output. The algorithm implemented a randomized greedy neighborhood search heuristic to find the optimal cardiac output quickly, without the need large for amounts of memory, and track a dynamic output.

The three dimensional output is shown in FIG. 14. The developed algorithm can find the optimal output of any three dimensional plot 100% of the time as long as it does not have any local maximums. The algorithm was tested on the graph of FIG. 14 starting from the point on the x, y plane (12,12). With over 1000 iterations (or starting points), the algorithm found the optimum in an average of 16.844, a maximum of 56, and a minimum of 4 attempts.

FIG. 15 illustrates a graph that shows the distribution of the number of attempts for the simulation algorithm. As shown in FIG. 15, the algorithm can find the optimal output efficiently for a three dimensional output. A particular benefit of the algorithm of the present invention is that as it is searching for the optimal output, it will continue to increase and never search farther than one step in the negative sloping direction. It will always return to the maximum output, thus preventing the contraction index from decreasing too much.

Another area that the algorithm of the present invention offers particular usefulness is in its ability to track a dynamic output. To test the algorithms ability to track the optimal output, the three dimensional plot of FIG. 14 was created to move randomly. This simulates the possibility of an ever changing cardiac condition. Once the algorithm found the optimal point on the plot, the algorithm was able to stay above 98% of the optimal output.

In a further experiment, data obtained from the hearts of six canine subjects was analyzed to study the effect of pacing site and heart rate on select measures of mechanical dyssynchrony.

"Mechanical dyssynchrony", "internal flow fraction" (IFF), and "mechanical dispersion" indices were calculated with the goal of relating dyssynchrony with either pacing site, biventricular (BV)—left ventricular (LV)—right atria (RA)—right ventricular (RV), or heart rate, 90 or 160 beats per minute (bpm). The "mechanical dyssynchrony" index quantifies the percentage of time that a change in a segmental LV volume was opposite the change in total LV volume. This was calculated for systole ($dP/dt_{max}$ to $dP/dt_{max}$) and diastole. The IFF index quantifies "segment-to-segment blood volume shifts, which do not result in effective filling or ejection." The "mechanical dispersion" index was calculated but found to be invalid for the particular data set. These indices were then cross-correlated with each other and also general measures of cardiac function such as external work (EW) and efficiency ($\eta$). Efficiency was defined as the following, where PVA is the pressure-volume area:

$$\eta = EW/PVA.$$

The results showed that there is a high variability between subjects (and within subjects) as to which pacing site (or heart rate) optimizes different measures of cardiac function. Accordingly, this analysis shows that "one size" does not fit all when it comes to pacing within the myocardium, and substantiates the benefits of the self-organizing leadless electrode stimulation delivery system and methods of the present invention for pacing on a more individual patient level.

While the above description is primarily directed to pacing electrodes for use in the heart for CRT, it is appreciated that the systems and methods described above are not limited to the CRT embodiment. The intelligent self-organizing leadless electrode stimulation delivery system, along with novel meta-material-based Van Atta array antennas of the present invention, may be used for a variety of different applications, including, but not limited to, use for pain management, deep brain stimulation, and spinal cord stimulation, or any other appropriate application where it is desirable to generate stimulation of biological tissues on or within the human body. It is anticipated that the meta-material-based Van Atta array antennas of the present invention may be useful for any application where energy harvesting and communication is desired for a miniaturized device (e.g. less than 1 cm in size).

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An electrode stimulation delivery system, comprising: (a) a plurality of wireless remote electrodes configured for implantation within a plurality of spaced apart locations in the tissue of a patient; (b) a control unit configured to be positioned at or subcutaneous to the patient's skin, the control unit comprising: a processor; an antenna configured for delivering electromagnetic energy in proximity to the plurality of wireless remote electrodes; and programming executable on the processor for wirelessly communicating to the plurality of wireless remote electrodes via the delivered electromagnetic energy to individually control activation of the plurality of wireless remote electrodes; (c) wherein each electrode in the plurality of wireless remote electrodes comprises a harvesting antenna configured to receive said electromagnetic energy to power activation of the plurality of wireless remote electrodes; and (d) wherein each electrode in the plurality of wireless remote electrodes comprises circuitry configured to modulate the harvesting antenna to generate a backscatter signal to communicate data back to the control unit.

2. The system of embodiment 1, wherein the harvesting antenna comprises a metamaterial-based biomimetic antenna.

3. The system of embodiment 1, wherein the harvesting antenna comprises a Van Atta array comprising at least one zero-phase transmission line.

4. The system of embodiment 3, wherein the at least one transmission line comprises a cascaded transmission line having negative phase segment and a negative phase segment configured to substantially cancel out a positive phase introduced by the positive phase segment.

5. The system of embodiment 3, wherein the negative phase segment comprises a metamaterial.

6. The system of embodiment 1, wherein the harvesting antenna comprises a Van Atta array configured for passive steering.

7. The system of embodiment 1, wherein the electromagnetic energy comprises RF energy.

8. The system of embodiment 1, wherein the plurality of wireless remote electrodes are configured to generate a pacing signal to pace tissue at said one or more locations.

9. The system of embodiment 8: wherein each electrode in the plurality of wireless remote electrodes comprises a sensor configured to measure a physiological characteristic at the one or more locations; wherein the programming is configured to receive data relating to the measured physiological characteristic; and wherein said data is used to generate a pacing sequence to control the timing of the individual wireless remote electrode pacing signals.

10. The system of embodiment 9: wherein the sensor comprises an accelerometer; and wherein the physiological characteristic comprises motion of the tissue at the one ore more locations.

11. The system of embodiment 9, wherein the plurality of wireless remote electrodes are configured to be implanted in the myocardium of the heart to pace a target region of the heart.

12. The system of embodiment 9: wherein the programming is configured to generate a contractility index of the tissue from said data; and wherein the programming is configured to perform an optimization search on the data to generate the pacing sequence.

13. The system of embodiment 1: wherein the control unit comprises a connected electrode coupled to the processor via a lead; and wherein the connected electrode comprises the antenna for delivering the electromagnetic energy to the plurality of wireless remote electrodes.

14. An electrode stimulation delivery system, comprising: (a) a plurality of wireless remote electrodes configured for implantation within a plurality of spaced apart locations in the tissue of a patient; (b) a control unit configured to be positioned at or subcutaneous to the patient's skin, the control unit comprising: a processor; an antenna configured for delivering electromagnetic energy in proximity to the plurality of wireless remote electrodes; and programming executable on the processor for wirelessly communicating to the plurality of wireless remote electrodes via the delivered electromagnetic energy to individually control activation of the plurality of wireless remote electrodes; (c) wherein each electrode in the plurality of wireless remote electrodes comprises a harvesting antenna configured to receive said electromagnetic energy to power activation of the plurality of wireless remote electrodes; and (d) wherein the harvesting antenna comprises a metamaterial-based biomimetic antenna.

15. The system of embodiment 14, wherein each of the plurality of wireless remote electrodes comprises circuitry configured to modulate the harvesting antenna to generate a backscatter signal to communicate data back to the control unit.

16. The system of embodiment 15, wherein the harvesting antenna comprises a passive-steering Van Atta array comprising at least one zero-phase transmission line.

17. The system of embodiment 16, wherein the at least one transmission line comprises a cascaded transmission line having negative phase segment and a negative phase segment configured to substantially cancel out a positive phase introduced by the positive phase segment.

18. The system of embodiment 17, wherein the negative phase segment comprises a metamaterial.

19. The system of embodiment 15, wherein the electromagnetic energy comprises RF energy.

20. The system of embodiment 15, wherein the plurality of wireless remote electrodes are configured to generate a pacing signal to pace tissue at said one or more locations.

21. The system of embodiment 20: wherein each electrode in the plurality of wireless remote electrodes comprises a sensor configured to measure a physiological characteristic at the one or more locations; wherein the programming is configured to receive data relating to the measured physiological characteristic; and wherein said data is used to generate a pacing sequence to control the timing of the individual wireless remote electrode pacing signals.

22. The system of embodiment 21: wherein the sensor comprises an accelerometer; and wherein the physiological characteristic comprises motion of the tissue at the one ore more locations.

23. The system of embodiment 21, wherein the plurality of wireless remote electrodes are configured to be implanted in the myocardium of the heart to pace a target region of the heart.

24. The system of embodiment 21: wherein the programming is configured to generate a contractility index of the tissue from said data; and wherein the programming is configured to perform an optimization search on the data to generate the pacing sequence.

25. The system of embodiment 15: wherein the control unit comprises a connected electrode coupled to the processor via a lead; and wherein the connected electrode comprises the antenna for delivering the electromagnetic energy to the plurality of wireless remote electrodes.

26. An electrode stimulation delivery system, comprising: (a) a plurality of wireless remote electrodes configured for implantation within a plurality of spaced apart locations in the tissue of a patient; (b) a control unit configured to be positioned at or subcutaneous to the patient's skin, the control unit comprising: a processor; an antenna configured for delivering electromagnetic energy in proximity to the plurality of wireless remote electrodes; and programming executable on the processor for wirelessly communicating to the plurality of wireless remote electrodes via the delivered electromagnetic energy to individually control activation of the plurality of wireless remote electrodes; (c) wherein each electrode in the plurality of wireless remote electrodes comprises a harvesting antenna configured to receive said electromagnetic energy to power activation of the plurality of wireless remote electrodes; and (d) wherein the harvesting antenna comprises a passive-steering Van Atta array comprising at least one zero-phase transmission line.

27. The system of embodiment 26, wherein each of the plurality of wireless remote electrodes comprises circuitry configured to modulate the harvesting antenna to generate a backscatter signal to communicate data back to the control unit.

28. The system of embodiment 26, wherein the at least one transmission line comprises a cascaded transmission line having negative phase segment and a negative phase segment configured to substantially cancel out a positive phase introduced by the positive phase segment.

29. The system of embodiment 28, wherein the negative phase segment comprises a metamaterial.

30. The system of embodiment 26, wherein the electromagnetic energy comprises RF energy.

31. The system of embodiment 26: wherein each electrode in the plurality of wireless remote electrodes is configured to generate a pacing signal to pace tissue at said one or more locations; wherein each electrode in the plurality of wireless remote electrodes comprises a sensor configured to measure a physiological characteristic at the one or more locations; wherein the programming is configured to receive data relating to the measured physiological characteristic; and wherein said data is used to generate a pacing sequence to control the timing of the individual wireless remote electrode pacing signals.

32. The system of embodiment 31: wherein the programming is configured to generate a contractility index of the tissue from said data; and wherein the programming is configured to perform an optimization search on the data to generate the pacing sequence.

33. The system of embodiment 26: wherein the control unit comprises a connected electrode coupled to the processor via a lead; and wherein the connected electrode comprises the antenna for delivering the electromagnetic energy to the plurality of wireless remote electrodes.

34. A method for delivering electrode stimulation to a patient, comprising: implanting a plurality of wireless remote electrodes within a plurality of spaced apart locations in the tissue of the patient; positioning a control unit configured at or subcutaneous to the patient's skin, and comprising; delivering electromagnetic energy from the control unit to a plurality of spaced apart locations in proximity to the plurality of wireless remote electrodes; and wirelessly communicating to the plurality of wireless remote electrodes via the delivered electromagnetic energy to individually control activation of the plurality of wireless remote electrodes; receiving said electromagnetic energy with a harvesting antenna on each of the plurality of wireless remote electrodes to power activation of the plurality of wireless remote electrodes; and modulating the harvesting antenna to generate a backscatter signal to communicate data back to the control unit.

35. The method of embodiment 34, wherein the harvesting antenna comprises a passive-steering Van Atta array comprising at least one zero-phase transmission line.

36. The method of embodiment 35, wherein the at least one transmission line comprises a cascaded transmission line having negative phase segment and a negative phase segment configured to substantially cancel out a positive phase introduced by the positive phase segment.

37. The method of embodiment 36, wherein the negative phase segment comprises a metamaterial.

38. The method of embodiment 34, wherein activation of the plurality of wireless remote electrodes comprises generating a pacing signal to pace tissue with the plurality of wireless remote electrodes at said one or more locations.

39. The method of embodiment 38, further comprising: measuring a physiological characteristic at the one or more locations; transmitting data relating to the measured physiological characteristic from each of the plurality of wireless remote electrodes to the control unit via the backscatter signal; and generating a pacing sequence to control the timing of the individual wireless remote electrode pacing signals.

40. The method of embodiment 39, further comprising: generating a contractility index of the tissue from said data; and performing an optimization search on the data to generate the pacing sequence.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An electrode stimulation delivery system, comprising:
   (a) a plurality of wireless remote electrodes configured for implantation within a plurality of spaced apart locations in the tissue of a patient;
   (b) a control unit configured to be positioned at or subcutaneous to the patient's skin, the control unit comprising:
      a processor;
      an antenna configured for delivering electromagnetic energy in proximity to the plurality of wireless remote electrodes; and
      programming executable on the processor for wirelessly communicating to the plurality of wireless remote electrodes via the delivered electromagnetic energy to individually control activation of the plurality of wireless remote electrodes;
   (c) wherein each electrode in the plurality of wireless remote electrodes comprises a harvesting antenna configured to receive said electromagnetic energy to power activation of the plurality of wireless remote electrodes; and
   (d) wherein each electrode in the plurality of wireless remote electrodes comprises circuitry configured to modulate the harvesting antenna to generate a backscatter signal to communicate data back to the control unit.

2. A system as recited in claim 1, wherein the harvesting antenna comprises a metamaterial-based biomimetic antenna.

3. A system as recited in claim 1, wherein the harvesting antenna comprises a Van Atta array comprising at least one zero-phase transmission line.

4. A system as recited in claim 3, wherein the at least one transmission line comprises a cascaded transmission line having negative phase segment and a negative phase segment configured to substantially cancel out a positive phase introduced by the positive phase segment.

5. A system as recited in claim 3, wherein the negative phase segment comprises a metamaterial.

6. A system as recited in claim 1, wherein the harvesting antenna comprises a Van Atta array configured for passive steering.

7. A system as recited in claim 1, wherein the electromagnetic energy comprises RF energy.

8. A system as recited in claim 1, wherein the plurality of wireless remote electrodes are configured to generate a pacing signal to pace tissue at said one or more locations.

9. A system as recited in claim 8:
   wherein each electrode in the plurality of wireless remote electrodes comprises a sensor configured to measure a physiological characteristic at the one or more locations;
   wherein the programming is configured to receive data relating to the measured physiological characteristic; and
   wherein said data is used to generate a pacing sequence to control the timing of the individual wireless remote electrode pacing signals.

10. A system as recited in claim 9:
    wherein the sensor comprises an accelerometer; and
    wherein the physiological characteristic comprises motion of the tissue at the one ore more locations.

11. A system as recited in claim 9, wherein the plurality of wireless remote electrodes are configured to be implanted in the myocardium of the heart to pace a target region of the heart.

12. A system as recited in claim 9:
    wherein the programming is configured to generate a contractility index of the tissue from said data; and
    wherein the programming is configured to perform an optimization search on the data to generate the pacing sequence.

13. A system as recited in claim 1:
    wherein the control unit comprises a connected electrode coupled to the processor via a lead; and
    wherein the connected electrode comprises the antenna for delivering the electromagnetic energy to the plurality of wireless remote electrodes.

14. An electrode stimulation delivery system, comprising:
    (a) a plurality of wireless remote electrodes configured for implantation within a plurality of spaced apart locations in the tissue of a patient;
    (b) a control unit configured to be positioned at or subcutaneous to the patient's skin, the control unit comprising:
       a processor;
       an antenna configured for delivering electromagnetic energy in proximity to the plurality of wireless remote electrodes; and
       programming executable on the processor for wirelessly communicating to the plurality of wireless remote electrodes via the delivered electromagnetic energy to individually control activation of the plurality of wireless remote electrodes;
    (c) wherein each electrode in the plurality of wireless remote electrodes comprises a harvesting antenna configured to receive said electromagnetic energy to power activation of the plurality of wireless remote electrodes; and
    (d) wherein the harvesting antenna comprises a metamaterial-based biomimetic antenna.

15. A system as recited in claim 14, wherein each of the plurality of wireless remote electrodes comprises circuitry configured to modulate the harvesting antenna to generate a backscatter signal to communicate data back to the control unit.

16. A system as recited in claim 15, wherein the harvesting antenna comprises a passive-steering Van Atta array comprising at least one zero-phase transmission line.

17. A system as recited in claim 16, wherein the at least one transmission line comprises a cascaded transmission line having negative phase segment and a negative phase segment configured to substantially cancel out a positive phase introduced by the positive phase segment.

18. A system as recited in claim 17, wherein the negative phase segment comprises a metamaterial.

19. A system as recited in claim 15, wherein the electromagnetic energy comprises RF energy.

20. A system as recited in claim 15, wherein the plurality of wireless remote electrodes are configured to generate a pacing signal to pace tissue at said one or more locations.

21. A system as recited in claim 20:
   wherein each electrode in the plurality of wireless remote electrodes comprises a sensor configured to measure a physiological characteristic at the one or more locations;
   wherein the programming is configured to receive data relating to the measured physiological characteristic; and
   wherein said data is used to generate a pacing sequence to control the timing of the individual wireless remote electrode pacing signals.

22. A system as recited in claim 21:
   wherein the sensor comprises an accelerometer; and
   wherein the physiological characteristic comprises motion of the tissue at the one ore more locations.

23. A system as recited in claim 21, wherein the plurality of wireless remote electrodes are configured to be implanted in the myocardium of the heart to pace a target region of the heart.

24. A system as recited in claim 21:
   wherein the programming is configured to generate a contractility index of the tissue from said data; and
   wherein the programming is configured to perform an optimization search on the data to generate the pacing sequence.

25. A system as recited in claim 15:
   wherein the control unit comprises a connected electrode coupled to the processor via a lead; and
   wherein the connected electrode comprises the antenna for delivering the electromagnetic energy to the plurality of wireless remote electrodes.

26. An electrode stimulation delivery system, comprising:
   (a) a plurality of wireless remote electrodes configured for implantation within a plurality of spaced apart locations in the tissue of a patient;
   (b) a control unit configured to be positioned at or subcutaneous to the patient's skin, the control unit comprising:
      a processor;
      an antenna configured for delivering electromagnetic energy in proximity to the plurality of wireless remote electrodes; and
      programming executable on the processor for wirelessly communicating to the plurality of wireless remote electrodes via the delivered electromagnetic energy to individually control activation of the plurality of wireless remote electrodes;
   (c) wherein each electrode in the plurality of wireless remote electrodes comprises a harvesting antenna configured to receive said electromagnetic energy to power activation of the plurality of wireless remote electrodes; and
   (d) wherein the harvesting antenna comprises a passive-steering Van Atta array comprising at least one zero-phase transmission line.

27. A system as recited in claim 26, wherein each of the plurality of wireless remote electrodes comprises circuitry configured to modulate the harvesting antenna to generate a backscatter signal to communicate data back to the control unit.

28. A system as recited in claim 26, wherein the at least one transmission line comprises a cascaded transmission line having negative phase segment and a negative phase segment configured to substantially cancel out a positive phase introduced by the positive phase segment.

29. A system as recited in claim 28, wherein the negative phase segment comprises a metamaterial.

30. A system as recited in claim 26, wherein the electromagnetic energy comprises RF energy.

31. A system as recited in claim 26:
   wherein each electrode in the plurality of wireless remote electrodes is configured to generate a pacing signal to pace tissue at said one or more locations;
   wherein each electrode in the plurality of wireless remote electrodes comprises a sensor configured to measure a physiological characteristic at the one or more locations;
   wherein the programming is configured to receive data relating to the measured physiological characteristic; and
   wherein said data is used to generate a pacing sequence to control the timing of the individual wireless remote electrode pacing signals.

32. A system as recited in claim 31:
   wherein the programming is configured to generate a contractility index of the tissue from said data; and
   wherein the programming is configured to perform an optimization search on the data to generate the pacing sequence.

33. A system as recited in claim 26:
   wherein the control unit comprises a connected electrode coupled to the processor via a lead; and
   wherein the connected electrode comprises the antenna for delivering the electromagnetic energy to the plurality of wireless remote electrodes.

34. A method for delivering electrode stimulation to a patient, comprising:
   implanting a plurality of wireless remote electrodes within a plurality of spaced apart locations in the tissue of the patient;
   positioning a control unit configured at or subcutaneous to the patient's skin, and comprising;
   delivering electromagnetic energy from the control unit to a plurality of spaced apart locations in proximity to the plurality of wireless remote electrodes; and
   wirelessly communicating to the plurality of wireless remote electrodes via the delivered electromagnetic energy to individually control activation of the plurality of wireless remote electrodes;
   receiving said electromagnetic energy with a harvesting antenna on each of the plurality of wireless remote electrodes to power activation of the plurality of wireless remote electrodes; and
   modulating the harvesting antenna to generate a backscatter signal to communicate data back to the control unit.

35. A method as recited in claim 34, wherein the harvesting antenna comprises a passive-steering Van Atta array comprising at least one zero-phase transmission line.

36. A method as recited in claim 35, wherein the at least one transmission line comprises a cascaded transmission line having negative phase segment and a negative phase segment configured to substantially cancel out a positive phase introduced by the positive phase segment.

37. A method as recited in claim 36, wherein the negative phase segment comprises a metamaterial.

38. A method as recited in claim 34, wherein activation of the plurality of wireless remote electrodes comprises generating a pacing signal to pace tissue with the plurality of wireless remote electrodes at said one or more locations.

39. A method as recited in claim 38, further comprising:
   measuring a physiological characteristic at the one or more locations;
   transmitting data relating to the measured physiological characteristic from each of the plurality of wireless remote electrodes to the control unit via the backscatter signal; and generating a pacing sequence to control the timing of the individual wireless remote electrode pacing signals.

40. A method as recited in claim 39, further comprising:

generating a contractility index of the tissue from said data; and performing an optimization search on the data to generate the pacing sequence.

* * * * *